United States Patent [19]

Murakami et al.

[11] Patent Number: 4,889,927
[45] Date of Patent: Dec. 26, 1989

[54] PRODUCTION PROCESS OF PHENYLGLYCOSIDES

[75] Inventors: Koji Murakami, Kyoto; Fumiaki Nakatsubo, Takayama; Yoshiaki Katsura, Kyoto; Motoo Matukura, Tokyo, all of Japan

[73] Assignee: Jujo Paper Co., Ltd., Tokyo, Japan

[21] Appl. No.: 163,839

[22] Filed: Mar. 3, 1988

[30] Foreign Application Priority Data

Mar. 4, 1987 [JP] Japan .................................. 62-49781

[51] Int. Cl.$^4$ ...................... C07H 15/20; C07H 13/06
[52] U.S. Cl. .................................. 536/18.6; 536/17.3; 536/17.6
[58] Field of Search ...................... 536/18.6, 17.3, 17.6

[56] References Cited

U.S. PATENT DOCUMENTS 4,362,720 12/1982 Limieux .............................. 536/17.3
4,432,973 2/1984 Picart ................................. 536/17.6

Primary Examiner—Ronald W. Griffin
Assistant Examiner—Pamela S. Webber
Attorney, Agent, or Firm—Sherman and Shalloway

[57] ABSTRACT

This invention concerns a process for producing phenolic substances with beneficial biological activities in a high yield, which comprises: subjecting a glycose of which an OH group at the 1 position is substituted for a halogen atom and of which other groups are substituted for acyl groups, and a phenol of which at least one of the ortho-positions in regard to phenolic OH groups is substituted to reaction with an alkali metal hydride in dimethylsulfoxide or dimethylformamide in the presence of or non-presence of a quat-ammonium salt and then hydrolyzing said acyl groups with an alkaline substance.

7 Claims, No Drawings

PRODUCTION PROCESS OF PHENYLGLYCOSIDES

FIELD OF THE INVENTION

This invention relates to a process for producing glycosides of a phenolic substance. More particularly, it concerns a process for producing a bonded product of a phenol and a glycose (hereinafter simply referred to as phenylglycoside) by coupling a phenolic OH group of the phenol and the 1 position of the glycose.

PRIOR ART

Traceable as they are, phenylglycosides exist widely in plants. Lots of studies have so far been reported on their isolation or purification. Nevertheless, studies on their biological activities have scarcely been reported. Recently, however, much more attention has been drawn to their development into medicines, partly because their toxicity is low. Along with the trend, reports on their biological activities are also on the increase.

For example, syringaresinol diglycoside, contained in the bark of *Liriodendron tulipifera* as liriodendrin or in the stems and roots of *Acanthpanax senticosus* as eleuterocido D, is reported to have a carcinostatic activity (J. Org. Chem., 45, 1327–1329 (1980)) or an activity of recovering phychogenic reaction (Jap. Patent laid-open publication SHO 59-116200). Also, pinoresinol diglycoside, contained in the bark of *Eucommia ulmoides*, is reported to have an action of inhibiting the activity of cyclic AMP diesterase phosphate (Phytochemistry, 23(6), 1207–1220 (1984).

As stated above, phenylglycosides are drawing special attention as a new physiologically active product and the establishment of an efficient production process is strongly desired.

As for their production process, there are considered a vegetable extraction-purification process and a bonding process of a glycose and a phenol part of aglycone by enzymatic (when glycose is used, glycosyltransferase is applied.) or chemical means.

The vegetable extraction-purification process, however, needs a considerable amount of cost and trouble in purification, yet its yield is low because the content of phenylglycosides in plants is small and impurities are extracted in plenty. The enzymatic process is narrowly confined to a limited group of substrates by the substrate specificity inherent to an enzymatic reaction which favors only a certain kind of enzyme. In other words, if several kinds of phenylglycosides are wanted, it is necessary to have a corresponding variety of enzymes beforehand, which mostly requires the preparation and selection of suitable enzymes from the beginning; thus, the process is inefficient in view of time and economy.

Also, as is well-known, the chemical bonding process only requires substituting the 1 position of a glycose with bromine after acetylating the glycose, and linking the Br-substituent with a phenol in the presence of silver salts such as silver carbonate in order to produce an objective phenylglycoside (Chem. Ber., 34, 957–981 (1901)). Silver salts in the process can be replaced with a special ion exchange resin (Synthesis, 823 (1979)). However, with this process, the yield of the objective product declines very much when the ortho-position of the phenolic OH group is substituted; consequently, it becomes particularly difficult to produce glycosides of 2,6-substituted phenols, such as syringaresinol diglycoside. For this, any studies on its production by means of chemical reaction have not been reported yet.

The present invention is, therefore, to provide an efficient production process of ortho-substituted phenylglycosides by the linkage of OH groups of a phenol with the 1 position of glycose; more particularly it is to provide a production process of phenylglycosides by the linkage of OH groups of a phenol, of which at least one of the orthopositions has a substituent, with the 1 position of glycose.

The present inventors thus made intensive studies on a production process of phenylglycosides having beneficial biological activities, particularly a production process of 2,6-substituted phenylglycosides of which efficient chemical production has not so far been established because of its difficulties, and finally accomplished the invention with the finding that an objective product, the linked product of the 1 position of a glycose and an OH group of a phenol can be obtained in a high yield when glycose of which an OH group at the 1 position is substituted for a halogen atom and of which other OH groups are substituted for acyl groups and a 2,6-substituted phenol are caused to react with one another in dimethylsulfoxide in the presence of an alkali metal hydride.

SUMMARY OF THE INVENTION

Accordingly, it is an object of this invention to provide a novel production process of phenylglycosides which comprises: subjecting a phenol of which at least one of the ortho-positions in regard to the phenolic hydroxy group is substituted (hereinafter simply referred to as ortho-substituted phenol), and a glycose of which the hydroxy group at the 1 position is substituted for a halogen atom and of which other hydroxy groups are substituted for acyl groups (hereinafter simply referred to as halogenoacyl glycose) to reaction in dimethylsulfoxide or dimethylformamide in the presence of an alkali metal hydride, adding water to the reaction mixture, conducting extraction by the use of a non-polar organic solvent that does not mix well with water, and treating the resulting extract with an alkaline substance. According to the invention, an ortho-substituted phenylglycoside, especially a 2,6-substituted phenylglycoside, of which any efficient production process has not yet been established, can be produced in a high yield.

DETAILED DESCRIPTION OF THE INVENTION

This invention will be described below in detail. As H. H. Kunz teaches (Liebing Annal. Chem., 41–84 (1982)), halogenoacyl glycose, one of the starting materials of this invention can be obtained in a high yield in the form of α-bromotetrapivaloylglycose through a reaction of D-glycose, for example, with an acylhalide such as pivaloylchloride in pyridine and a subsequent reaction with hydrogen halides such as hydrogen bromide. One mole of an ortho-substituted phenol and one mole or more than one mole of the halogenoacyl glycose are made react with one another in dimethylsulfoxide or dimethylformamide in the presence of one mole or more than one mole of an alkali metal hydride. In this case, it is recommended to mix well the ortho-substituted phenol and the alkali metal hydride in dimethylslufoxide or dimethylformamide with stirring and to dissolve the halogenoacyl glycose in a small amount of a good solvent such as dichloroethane separately then add the glycose solution to the phenol mixture.

For causing the reaction, it can make do with room temperatures; too high a temperature is improper because unfavorable side reactions are likely to occur resulting in a decline in the yield of the product. The reaction commonly progresses very fast, so that 30–60 minutes will suffice for it.

In the case of phenol, such as syringaresinol, the yield of the product depends on the kind of acyl groups that protect the glycose hydroxy groups. When the alkyl group bonded with a carbonyl carbon of the acyl group is a tertiary one, the yield of the objective phenylglycoside attains 90 percent, the highest level of all. A secondary alkyl group is the next while in the case of a primary alkyl group, the yield decreases to about 50 percent. In view of the good and stable yield, an acyl group possessing tert-alkyl groups, such as a pivaloyl group, is therefore most desirable of all. Also, adding a quat-ammonium salt, such as triethylbenzylammonium bromide or tetra-n-butylammonium, to ortho-substituted phenol by an equivalent mole or more makes the yield increase. Moreover, when dimethylsulfoxide is employed as a solvent, it gives a better effect to the yield than dimethylformamide.

Among available alkali metal hydrides are lithium hydride, sodium hydride, potassium hydride and so forth, but sodium hydride is cheap and most suitable of all.

For isolating an objective acylated phenylglycoside from the reaction mixture, partition extraction by the use of water and a weak polar organic solvent, such as ethylacetate or ether and the subsequent purification through a conventional well-known chromatography are useful. An isolated pure acylated phenylglycoside is dissolved in alcohol, such as methanol or ethanol and then treated with an alkaline solution, such as sodium hydroxide or potassium hydroxide.

The acyl group is rapidly hydrolyzed; the acylated product turns into a phenylglycoside. Preliminary isolation of an acylated phenylglycoside is not always necessary for the alkaline hydrolysis. After the extraction, acylated phenylglycoside may be hydrolyzed directly with the isolation process skipped.

For isolating a pure phenylglycoside from the hydrolyzed solution, the removal of a cation is conducted by using a cation exchange resin. After that, the de-cationized solution is concentrated and then rinsed with ether, or a phenylglycoside contained in the hydrolyzed solution is made to absorb to an absorbing resin comprising a styrene-divinyl benzene copolymer, such as Amberlita XA D-2 produced by Organo Co., Ltd. and then eluted from the absorbing resin by using a solvent, such as alcohol.

According to the invention, ortho-substituted phenylglycosides can be produced with high efficiency. In particular, 2,6-substituted phenylglycosides, of which production used to be difficult with conventional chemical processes, can be obtained in a high yield, exclusively in the β-form.

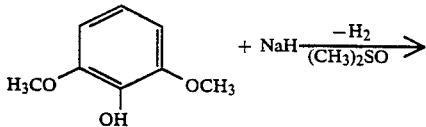

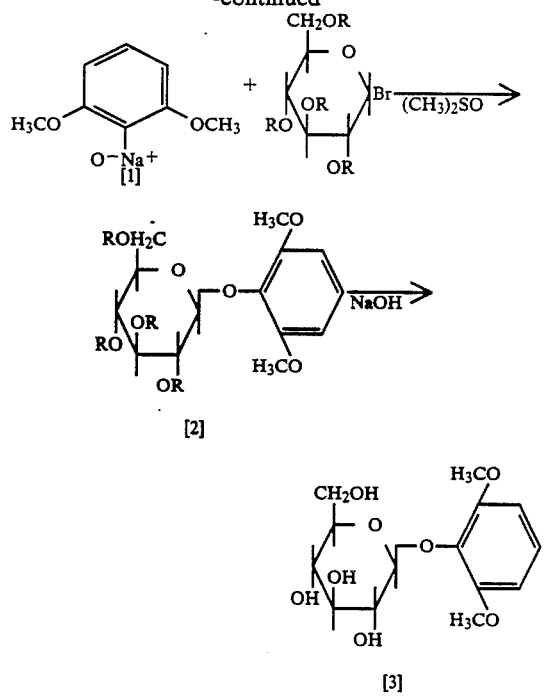

(In the above reaction formula, R stands for $(CH_3)_3CC=O$.)

In the case that the acyl group is pivaloyl group, the halogen is Br, the phenol is 2,6-dimethoxyphenol, and the alkali metal hydride is sodium hydride, the reaction mechanism in dimethylsulfoxide can be assumed like the above. In a dimethylsulfoxide solution, the reaction first takes place between the phenol and the sodium hydride, with the result that sodium phenolate [1] appears.

Secondly, $(CH_3)_2SO$, which is in the form of $(CH_3)_2S^+O,^-$ attacks the 1 position of α-bromotetrapivaloylglycose and gives an intermediate product, from which $Br^-$ is released, and forms NaBr. When $(CH_3)_2SO$ is released from the intermediate product as well, the pivaloyl group at the 2 position of the glycose, in the form of $(CH_3)_3CC^+O^-$, attacks a plus-charged carbon at the 1 position of the phenol and forms a 5-membered cyclic acylooxonium ion. Phenoxide ion attacks the cyclic acylooxonium ion, exclusively from above the pyranose ring and opens the 5-membered ring so as to return to pivaloyl groups and form β-phenylglycoside [2]. The β-glucoside [2] gives a liberated phenylglycoside [3] quantitatively, as its pivaloyl group is hydrolyzed by sodium hydroxide.

In the prescribed condition of the invention, 2,6-substituted phenol gives the highest yield of all; however, the reason for this is still unknown. A complete elucidation of the reason has to be expected from studies in the future. Anyway, as long as there is a fact in the production process that dimethoxyphenol gives far better yield than monomethyoxyphenol, and non-substituted phenol gives almost no phenylglycoside, 2,6-substituted phenol is considered to have such favorable properties as helping the formation of phenoxide ion, increasing the attackability of phenoxide ion against acylooxonium ion, and stabilizing an intermediate product. Moreover, the addition of a quat-ammonium salt is considered to increase the activity of phenoxide ion, and augment the yield of the product as a result. The reaction is also considered a progress similarly in both the solvents: dimethylformamide and dimethylsulfoxide. Furthermore, the fact that the yield declines in the order of tertiary, secondary and primary acyl groups in the case of producing complex structured 2,6-substituted phenylglycosides, such as syringaresinol may be accountable for the difference in the electron donative power among different acyl groups.

EXAMPLE 1

4.18 g of syringaresinol and 2.72 g of triethylbenzylammonium bromide were dissolved in 200 ml of dimethylsulfoxide. The solution was mixed with 2.8 g of sodium hydride of 60 percent purity (in oil) with stirring for 15 minutes. Next, 23.2 g of α-bromotetrapivaloylglycose were dissolved in 50 ml of dichloroethane. This solution was mixed with the above dimethylsulfoxide solution with stirring for about 30 minutes.

After that, the mixture was moved to a separating funnel; 100 ml of 1N-HCl was added to it to rinse with shaking. Three cycles of washing with water followed the rinsing with HCl. Sodium sulfate anhydride was added to drying. After drying, filtration and rinsing were conducted. Filtered solution and rinsing solution were put together and distilled to remove the mixed solvents. Residual syrup was dissolved in 190 ml of ethanol and stirring was continued for 4 hours after 80 ml of 2N sodium hydroxide was added. Resinous material was filtered off 40 g of anion exchange resin, Amberlite IR-120B, was added with stirring for 15 minutes.

Filtered solution was concentrated and dried, and then extraction and rinsing were made by adding 50 ml of ethylether, which was to be removed later. After 20 ml of water were added and stirring was made for about an hour, a crude crystal appeared, and which was separated by filtration. The dried crude crystal weighted 7.40 g. It was caused to re-crystallized in ethanol aqueous solution; as a result, a colorless needle crystal was obtained. Concentration and re-crystallization of the mother solution were repeated and 6.70 g of a colorless needle crystal were obtained in total.

Infrared adsorption spectrum of the produced crystal closely agreed with that of syringaresinol diglycoside isolated from the bark of Liriodendron tulipifera.

EXAMPLE 2

In compliance with the same conditions and process as in Example 1, 4.18 g of syringaresinol were dissolved in 200 ml of dimethylsulfoxide, and then 2.8 g of sodium hydride of 60 percent purity were added thereto with stirring. A mixture prepared by dissolving 23.2 g of α-bromotetrapivaloylglucose in 50 ml of dichloroethane was further added thereto with continous stirring.

After that, the reaction mixture was moved to a separating funnel in the same way as in Example 1. After rinsing was made with 1N HCl and water, sodium sulfate anhydride was added for drying and then the solvent was removed by distillation. The residual product was fed into a column, packed with 500 of silica gel C-200, product of Wako Pure Chemicals Co., Ltd. and a solvent mixture composed of n-hexane and ethylacetate in the ratio of 4:1 by volume. Objective product was collected under the monitoring of the silica gel thin layer chromatography. An obtained fraction gave an almost colorless solid product after the removal of the solvent.

The solid product was dissolved in ethanol according to the same condition and process as in Example 1, and treated with caustic soda, and then with Amberlite 120B. The filtered solution was concentrated and dried. The remaining crude crystal was rinsed with ether, and re-crystallized in ethanol aqueous solution.

Finally 5.95 g of a colorless needle crystal were obtained. Infrared absorption spectrum of the crystal closely agreed with that of syringaresinol diglucoside produced from the bark of Liriodendron tulipifera.

EXAMPLE 3

After 4.18 g of syringaresinol was dissolved in 200 of dimethylformamide, reaction, rinsing, hydrolysis, decationization, and condensation were carried out in the same condition and order as in Example 1. As a result, 5.1 g of crude crystal were obtained. The crystal was rinsed with ether and recrystalized in ethanol aqueous solution. Colorless needle crystal finally apeared.

Infrared absorption spectrum of the needle crystal completely agreed with that of syringaresinol diglycoside produced from the bark of Lirodendron tulipifera.

EXAMPLE 4

According to the same process as in Examples 1 and 2, 2,6-dimethoxyphenol, 2-methoxyphenol and phenol, and bromoacylated glycose, xylose, mannose, and galactose were caused to react in the presence of triethylbenzylammonium bromide so that phenylglycosides were prepered.

The following Tables 1, 2, and 3 give the results, from which it can be recognized that 2,6-substituted phenylglycoside was prepared in a high yield according to the invention.

TABLE 1

Different Phenols and Their Effect in the Yield of Corresponding Phenylglycosides

| Phenols | Phenylglycosides (yield %) |
|---|---|
| 2,6-dimethoxyphenol | 92.5 |
| 2-methoxyphenol | 45.5 |
| phenol | trace |

TABLE 2

Different Acyl groups and Their Effect in the Yield of Phenylglycosides

| Acyl groups | 2,6-dimethoxyphenyl-glycoside (yield %) | Syringaresinol diglycoside (yield %) |
|---|---|---|
| $(CH_3)_3CCO$ | 92.5 | 90.3 |
| $(CH_3)_2CHCO$ | 87.0 | 69.5 |
| $CH_3CO$ | 83.6 | 49.6 |

TABLE 3

Different Monosaccharides and Their Effect in the Yield Corresponding 2,6-dimethoxphenylglycosides

| Monosaccharides | 2,6-dimethoxyphenylglycosides |
|---|---|
| glycose | 96.0 (yield %) |
| xylose | 88.4 |
| mannose | 92.0 |
| galactose | 94.6 |

As best seen from the above, according to the invention, 2,6-substituted phenylglycosides, such as syringaresinol diglycoside, having useful biological activities, of which chemical production has so far been difficult, can be obtained in a high yield. Additionally, the production can be conducted in mild conditions and require neither special equipment nor troublesome operations; therefore, commercialization is quite simple.

We claim:

1. A process for production of 2,6-disubstituted-phenylglycosides, which comprises: reacting a glycose, of which the hydroxy group at the 1 position is substituted by a halogen atom and of which the other hydroxy groups are protected by tertiary acyl groups, a phenol, of which both of the ortho-positions in regard to the phenolic hydroxy group are substituted by substituents and an alkali metal hydride in dimethylsulfoxide or dimethylformamide in the presence or non-presence of a quaternary-ammonium salt; and then hydrolyzing said acyl groups with an alkaline substance.

2. The process for the production of phenylglycosides according to claim 1, wherein there is used a glycose of which a hydroxy group at the 1 position is substituted by a chlorine, bromine, or iodine atom.

3. The process for the production of phenylglycosides according to claim 1, characterized by employing α-bromotetrapivaloylglycose as the glycose defined in claim 1.

4. The process of the production of phenylglycosides according to claim 1, characterized by employing any one alkali metal hydride selected from the group consisting of lithium hydride, sodium hydride, and potassium hydride.

5. The process for the production of phenylglycosides according to claim 1, characterized by employing sodium hydride as an alkali metal hydride in claim 1.

6. The process for the production of phenylglycosides according to claim 1, characterized by subjecting one mole of a 2,6-disubstituted phenol and at least one mole of halogenoacylglycose to reaction.

7. The process for the production of phenylglycosides according to claim 1, characterized by employing any one quaternary-ammonium salt selected from the group consisting of triethylbenzylammonium bromide and tetra-n-butylammonium.

* * * * *